(12) United States Patent
Ferey et al.

(10) Patent No.: US 8,497,375 B2
(45) Date of Patent: Jul. 30, 2013

(54) METHOD OF SYNTHESIS OF FERROQUINE BY CONVERGENT REDUCTIVE AMINATION

(71) Applicant: Sanofi, Paris (FR)

(72) Inventors: Vincent Ferey, Paris (FR); Julia Mateos-Caro, Paris (FR); Régis Mondiere, Paris (FR); Philippe Vayron, Paris (FR); Sylvie Vigne, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/709,710

(22) Filed: Dec. 10, 2012

(65) Prior Publication Data

US 2013/0096306 A1  Apr. 18, 2013

Related U.S. Application Data

(63) Continuation of application No. PCT/IB2011/052536, filed on Jun. 10, 2011.

(30) Foreign Application Priority Data

Jun. 11, 2010 (FR) ..................... 10 54625

(51) Int. Cl.
*C07F 15/00* (2006.01)

(52) U.S. Cl.
USPC .......................................................... 546/4

(58) Field of Classification Search
None
See application file for complete search history.

(56) References Cited

U.S. PATENT DOCUMENTS 6,127,543 A   10/2000   Brocard et al.

FOREIGN PATENT DOCUMENTS

WO   WO 96/35698      11/1996
WO   WO 2011/154923    6/2011

OTHER PUBLICATIONS

Barends, et al., In Vitro Activity of Ferroquine (SSR 97193) Against *Plasmodium falciparum* Isolates from the Thai-Burmese Border, Malaria Journal, (2007), vol. 6, No. 81, pp. 1-5.
Biot, et al., Novel Metallocenic Compounds as Antimalarial Agents. Study of the Position of Ferrocene in Chloroquine, Journal of Organometallic Chemistry, vol. 589, (1999), pp. 59-65.
Biot, et al., Easily Synthesized Antimalarial Ferrocene Triazacyclononane Quinoline Conjugates, Journal of Organometallic Chemistry, vol. 689, (2004), pp. 4678-4683.
Biot, et al., Synthesis and Antimalarial Activity in Vitro and In Vivo of a New Ferrocene-Chloroquine Analogue, J. Med. Chem., (1997), vol. 40, pp. 3715-3718.
Daher, et al., Assessment of *Plasmodium falciparum* Resistance to Ferroquine (SSR97193) in Field Isolates and in W2 Strain Under Pressure, Malaria Journal, (2006), vol. 5, No. 11, pp. 1-8.
Domarle, et al., In Vitro Antimalarial Activity of a New Organorrietallic Analog, Ferrocene-Chloroquine, Antimicrobial Agents and Chemotherapy, (1998), pp. 540-544.

*Primary Examiner* — Janet Andres
*Assistant Examiner* — Heidi Reese
(74) *Attorney, Agent, or Firm* — Ronald G. Ort

(57) ABSTRACT

The invention relates to a method of synthesis of ferroquine of formula (F) or of its metabolite of formula (Fm):

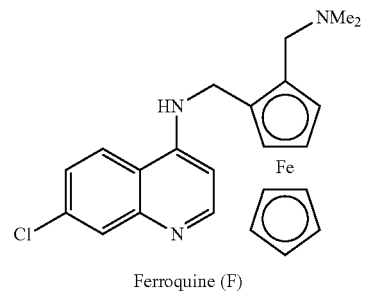

Ferroquine (F)

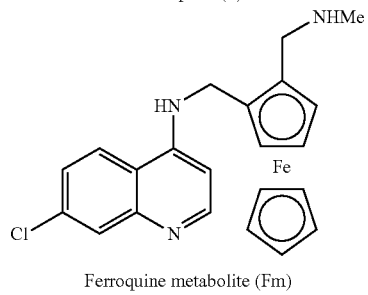

Ferroquine metabolite (Fm)

comprising a reaction of reductive amination, said reaction comprising:
(i) a stage of condensation of an aldehyde-amino ferrocene of formula (III), in which R represents a hydrogen atom or a methyl group, with 7-chloroquinolin-4-amine as shown below,

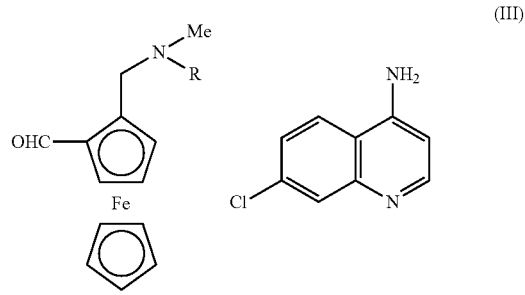

(III)

followed by
(ii) a stage of reduction of the product of condensation obtained in the preceding stage and
(iii) then a stage of hydrolysis of the reaction mixture in the presence of an aqueous solution of ammonia or of citric acid.

21 Claims, No Drawings

METHOD OF SYNTHESIS OF FERROQUINE BY CONVERGENT REDUCTIVE AMINATION

The present invention relates to a new method of synthesis of ferroquine particularly useful for the treatment and/or prevention of malaria.

Malaria is one of the primary infectious causes of mortality in the world and affects annually more than 500 million people, among whom 3 million die each year.

Four types of parasites of the genus Plasmodium carried by Anopheles mosquitoes, spread malaria. Plasmodium falciparum, widespread in Africa, is the most virulent parasite among them and is responsible for the deadly forms of the disease.

Among the active principles against Plasmodium falciparum, chloroquine is an antimalarial of the family of the 4-aminoquinolines, widely used, but for which resistances have developed since the 1960s. Artemisinin then made its appearance and proves effective against forms of plasmodia resistant to chloroquine. However, since 2006, the WHO noted the risk of resistance of the parasite to this molecule. It was in this same year 2006 that a new molecule, ferroquine, was discovered, displaying efficacy against the strains of Plasmodium falciparum resistant to chloroquine described in Malaria Journal 2006, 5: 11 and Malaria Journal 2007, 6: 81.

Ferroquine is an organometallic complex of iron. In particular, it is a derivative of 4-aminoquinoline coupled to a ferrocene nucleus.

Ferroquine, also called ferrocene-chloroquine or ferrochloroquine, corresponds to 7-chloro-4-[(2-N,N-dimethylaminomethyl)ferrocenylmethylamino]quinoline. It can be in the form of free base, but also in the form of salt, of hydrate or of solvate (these last being defined as associations or combinations of ferroquine with, respectively, one or more molecules of water or of solvent). Advantageously, ferroquine is used in the form of free base.

Ferroquine of formula (F) in the form of free base and its principal metabolite (Fm) are represented below in scheme 1.

Ferroquine is described in patent WO 96/35698, as well as in scientific articles such as J. Med. Chem., 1997, 40, 3715-3718, Antimicrob. Agents Chemother., 1998, 42, 540-544, J. Org. Chem., 1999, 589, 59-65 and J. Organometallic Chem., 2004, 689, 4678-4682.

Scheme 1

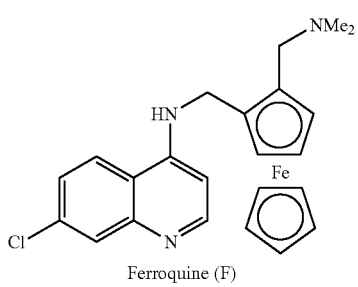

Ferroquine (F)

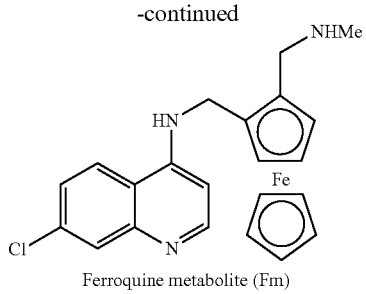

Ferroquine metabolite (Fm)

The known method for the manufacture of ferroquine, partially represented in scheme 2 below, consists in synthesizing firstly 1-[(dimethylamino)methyl]-2-formyl-ferrocene from (dimethylamino)methyl-ferrocene with a yield of about 85%, then in preparing the corresponding intermediate oxime, and finally in carrying out reduction of this oxime which leads to obtaining 1-(aminomethyl)-2-[(dimethylamino)methyl]-ferrocene which can be isolated in the form of dihydrochloride. The yield of synthesis of the dihydrochloride 1-(aminomethyl)-2-[(dimethylamino)methyl]-ferrocene relative to 1-[(dimethylamino)methyl]-2-formyl-ferrocene is 55-65%.

Scheme 2

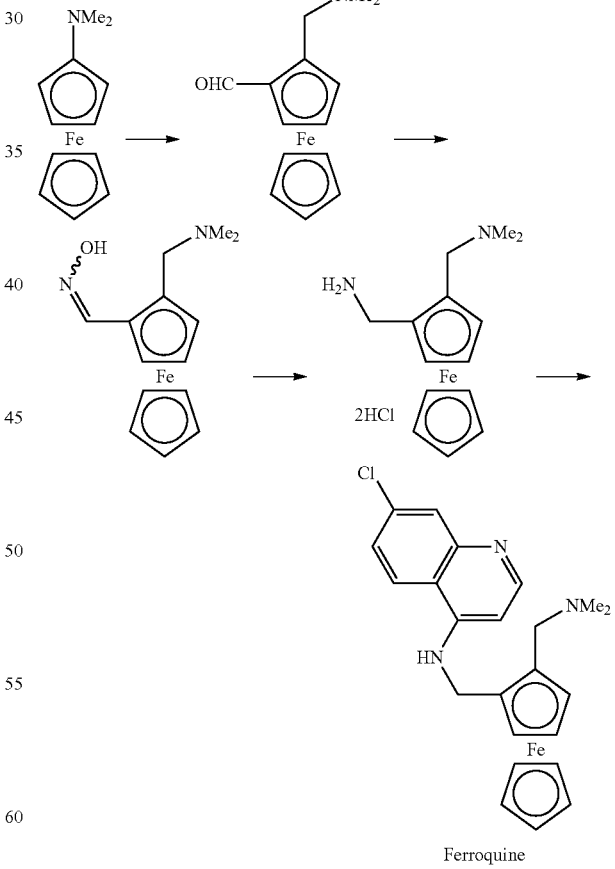

Ferroquine

This latter reaction sequence comprises firstly the condensation reaction of 1-[(dimethylamino)methyl]-2-formyl-ferrocene with the reagent hydroxylamine to lead to production of the corresponding oxime. Then, reduction of the oxime function to amine by the metal hydride $LiAlH_4$ is carried out in rigorously anhydrous medium in order to form after hydrolysis 1-(aminomethyl)-2-[(dimethylamino)methyl]-ferrocene, isolated in the form of dihydrochloride. The latter hereinafter is also called dihydrochloride of diamino ferrocene which is a salt of 1-(aminomethyl)-2-[(dimethylamino)methyl]-ferrocene, itself hereinafter called diamino ferrocene or diamino ferrocene in the form of free base.

Once diamino ferrocene in the form of free base, or its salt of dihydrochloride is obtained, the latter can be reacted in the presence of (i) a base, such as for example soda or triethylamine and (ii) of 4,7-dichloroquinoline in order to synthesize ferroquine by aromatic nucleophilic substitution. This stage of the synthesis of ferroquine, known and described, is transposable to diamine ferrocene in the form of free base. The ferroquine thus obtained can then undergo a purification in order to obtain pure ferroquine.

However, there are many drawbacks connected with this method. In fact, the risks associated with the use of reagents such as hydroxylamine (unstable and explosive) and $LiAlH_4$ (inflammable and very reactive in damp conditions), as well as the use of an intermediate such as the oxime, (thermally unstable) do not allow envisaging the production of ferroquine in adequate conditions of hygiene and safety from an industrial standpoint.

Moreover, the use of particularly expensive reagents, such as for example $LiAlH_4$, and the low productivity of this method (large number of stages, dilutions) contribute significantly to the cost of manufacture of Ferroquine. Now, with the aim of permitting access to ferroquine for the greatest number in poor countries, which moreover have the greatest need for it, it is essential to minimize the cost of manufacture of an active principle such as this in order to reduce significantly the cost price of antimalarial treatment.

The applicant has now found a new method of synthesis of ferroquine of formula (F) or of its metabolite of formula (Fm) making it possible to form said ferroquine or said metabolite directly from aldehyde-amino ferrocene of formula (III), in which R represents a hydrogen atom or a methyl group (Me), and from 7-chloroquinolin-4-amine.

The method according to the invention therefore consists in coupling the aldehyde-amino ferrocene of formula (III) with 7-chloroquinolin-4-amine according to a reaction of reductive amination, called convergent, represented in scheme 3.

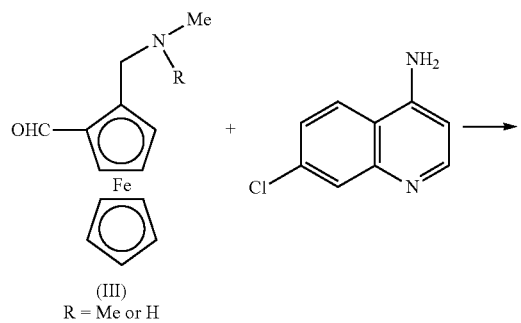

Scheme 3

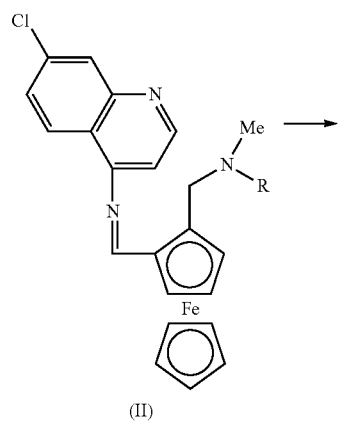

(II)

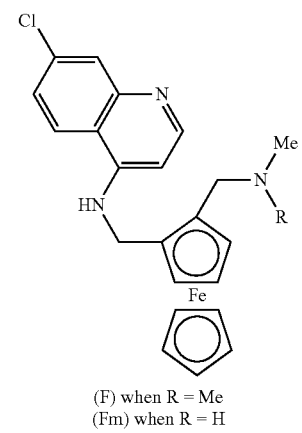

(F) when R = Me
(Fm) when R = H

The reaction of reductive amination therefore takes place in a single stage but in several steps:

Firstly, 7-chloroquinolin-4-amine reacts with the carbonyl function of aldehyde-amino ferrocene of formula (III), to form an imine function (which can be protonated to iminium if the reaction mixture is acid) according to a reaction of condensation, with liberation of a molecule of water;

Secondly, the imine function of the imino ferrocene intermediate of formula (II), or if applicable of the iminium, is then reduced by a hydride donor.

Thirdly, the reaction mixture is hydrolyzed in the presence of an aqueous solution of ammonia or else of citric acid, in order to destroy the excess hydride employed and permit isolation of ferroquine (F) or of its metabolite (Fm).

The imino ferrocene intermediate of formula (II) or the corresponding iminium, not shown, does not to be isolated in contrast to the oxime-amino ferrocene of the prior art represented above. The reaction of convergent reductive amination according to the present invention can therefore be carried out as a so-called one pot process. Moreover, the imino ferrocene intermediate of formula (II) not being stable in conditions of analysis by liquid phase chromatography, its formation can be followed qualitatively by thin-layer chromatography or in situ by Infrared analysis.

The invention therefore relates to a method of synthesis of ferroquine of formula (F) or of its metabolite of formula (Fm):

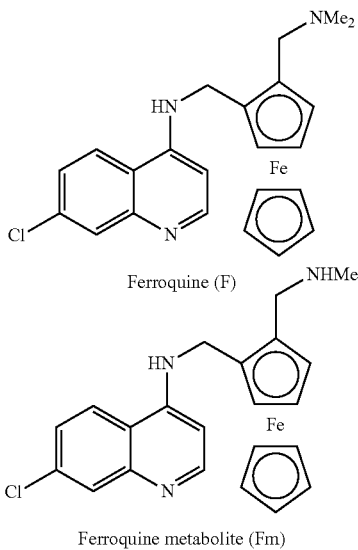

Ferroquine (F)

Ferroquine metabolite (Fm)

comprising a reaction of reductive amination, in which reaction:

(i) the aldehyde-amino ferrocene of formula (III),

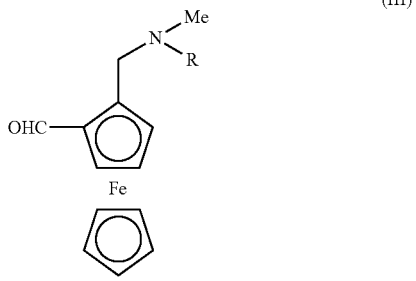

(III)

in which R represents a hydrogen atom or a methyl group, is condensed with 7-chloroquinolin-4-amine

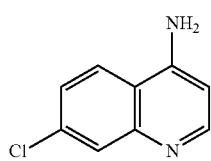

(ii) the product of condensation thus obtained of formula (II),

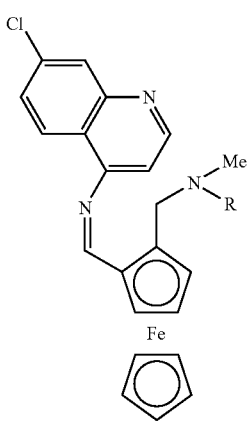

(II)

with R representing a hydrogen atom or a methyl group, is reduced, (iii) the reaction mixture is hydrolyzed.

After hydrolysis, the ferroquine of formula (F) and its metabolite of formula (Fm) are isolated.

According to the present invention, said compounds 7-chloroquinolin-4-amine and aldehyde-amino ferrocene of formula (III) are advantageously present in stoichiometric proportion.

The reaction of reductive amination according to the invention takes place in the presence of at least one reaction solvent suitable both for said stage of condensation and for said stage of reduction. This reaction solvent is selected from the protic and aprotic solvents, such as for example ethanol, isopropanol, toluene, THF, dichloromethane and mixtures thereof. The protic solvents are particularly advantageous. We may thus mention ethanol and/or isopropanol, advantageously isopropanol, as reaction solvent permitting particularly advantageous yields of reductive amination to be obtained.

The Stage of Condensation

The stage of condensation of 7-chloroquinolin-4-amine with the aldehyde-amino ferrocene of formula (III) takes place in the presence of:

at least one Lewis acid, or at least one Brønsted base or a Brønsted acid.

This stage can preferably take place under azeotropic distillation of the reaction solvent of said stage of condensation or in the presence of at least one drying agent.

The stage of condensation of 7-chloroquinolin-4-amine with aldehyde-amino ferrocene of formula (III) can take place in the presence of at least one Lewis acid such as $Ti(OiPr)_4$, $TiCl_4$, $FeCl_3$, $ZnCl_2$, $AlCl_3$ and $BF_3$. The Lewis acid $BF_3$ can be in the form of a complex such as for example $BF_3.OEt_2$ and $BF_3.S(Me)_2$.

Thus, in the method according to the invention, the Lewis acid is selected from $Ti(OiPr)_4$, $TiCl_4$, $FeCl_3$, $ZnCl_2$, $AlCl_3$, $BF_3$, $BF_3.OEt_2$ and $BF_3.S(Me)_2$.

According to a particularly advantageous embodiment, the Lewis acid is $Ti(OiPr)_4$.

The Lewis acid can be used in stoichiometric amount or in excess.

Advantageously, the Lewis acid is used in an amount between 1 and 2 equivalents, even advantageously the Lewis acid is present at the level of 1 equivalent.

According to a particularly advantageous embodiment of the stage of condensation in the presence of the Lewis acid $Ti(OiPr)_4$, 7-chloroquinolin-4-amine, the aldehyde-amino ferrocene of formula (III) and said Lewis acid are present at a level of 1 equivalent each. In this case, the reaction solvent is preferably isopropanol.

The stage of condensation of 7-chloroquinolin-4-amine with aldehyde-amino ferrocene of formula (III) can take place in the presence of at least one Brønsted acid or a Brønsted base selected from acetic acid, trifluoroacetic acid, methanesulfonic acid, para-toluenesulfonic acid, $H_2SO_4$, $H_3PO_4$, $HNO_3$, piperidine and proline.

Advantageously it is para-toluenesulfonic acid or piperidine, even more advantageously it is para-toluenesulfonic acid.

According to an embodiment particularly relating to the stage of condensation in the presence of a Brønsted acid, advantageously para-toluenesulfonic acid, said stage of condensation takes place under azeotropic distillation of the reaction solvent. In this case, the reaction solvent is preferably toluene.

Since the stage of condensation of an equivalent of 7-chloroquinolin-4-amine with an equivalent of aldehyde-amino ferrocene of formula (III) is accompanied by the liberation of an equivalent of water, it is conceivable to trap the water thus formed by means of a drying agent or to evacuate this water from the reaction mixture by carrying out an azeotropic distillation with a suitable reaction solvent such as for example the protic and aprotic solvents enumerated above. This azeotropic distillation can be effected, for example by means of a Dean-Stark, during said stage of condensation, with the aim of displacing the equilibrium toward formation of the imino ferrocene intermediate (II), or iminium if applicable. Said azeotropic distillation can optionally take place at reduced pressure, for example, at a pressure in the range from 100 to 300 mbar.

The stage of condensation of 7-chloroquinolin-4-amine with the aldehyde-amino ferrocene of formula (III) can therefore take place in the presence of at least one drying agent or can take place under azeotropic distillation of the reaction solvent from said reaction of condensation.

As drying agent mention may be made of alumina, a molecular sieve 3 Å, $MgSO_4$ and $Na_2SO_4$.

Advantageously, it is a molecular sieve 3 Å.

The Stage of Reduction

The stage of reduction of the intermediate obtained at the end of the stage of condensation between 7-chloroquinolin-4-amine with the aldehyde-amino ferrocene of formula (III), is carried out in the presence of at least one hydride donor.

The hydride donors known in the state of the art, particularly advantageous for said reaction of reduction, are hydrogen in the presence of a catalyst (transition metal, optionally in the form of complex) and metal hydrides. The metal hydrides are selected from borohydrides of sodium, of potassium, of lithium or of zinc and are optionally coupled to at least one additive selected from LiCl, $CaCl_2$, $MgCl_2$, $ZnCl_2$ and $NEt_3$. Said borohydrides of sodium, of potassium, of lithium or of zinc are selected from $NaBH(OAc)_3$, $NaBH_3CN$, $NaBH_4$, $KBH_4$, $LiBH_4$ and $Zn(BH_4)_2$ coupled or not to said additive.

$NaBH_4$, $KBH_4$ and $LiBH_4$, coupled or not to said additive prove particularly advantageous for carrying out the reaction of reduction of the imino ferrocene intermediate of formula (II), if necessary of the corresponding iminium, not shown.

Hydrolysis

The stage of hydrolysis takes place in the presence of an aqueous solution of ammonia or of citric acid.

When $Ti(OiPr)_4$ is used as Lewis acid during the stage of condensation, hydrolysis of the reaction mixture in the presence of an aqueous solution of citric acid is a particularly advantageous embodiment since it permits removing the titanium salts at the level of the aqueous phases and thus permits avoiding very difficult filtration of these salts.

According to one embodiment of the method of the invention, the stage of condensation takes place in the presence of toluene as reaction solvent, optionally under azeotropic distillation, for example by means of a Dean-Stark. In this embodiment, the stage of reduction preferably takes place in the presence of $NaBH_4$.

According to one embodiment of the method of the invention, the stage of condensation takes place in the presence of molecular sieve 3 Å as drying agent. In this embodiment, the stage of reduction preferably takes place in the presence of $NaBH_4$.

According to one embodiment of the method of the invention concerning the stage of condensation in the presence of a Brønsted acid, advantageously para-toluenesulfonic acid, said stage of condensation takes place under azeotropic distillation of the reaction solvent. This solvent is advantageously toluene. In this embodiment, the reaction of reduction preferably takes place in the presence of $NaBH_4$.

According to one embodiment of the method of the invention concerning the stage of condensation in the presence of toluene as reaction solvent, said stage of condensation takes place under azeotropic distillation. In this embodiment, the stage of reduction preferably takes place in the presence of $NaBH_4$.

According to one embodiment of the method of the invention concerning the stage of condensation in the presence of a Lewis acid, advantageously titanium tetra-isopropylate, the reaction solvent is preferably isopropanol.

According to one embodiment of the method of the invention, the stage of condensation takes place in the presence of 1 to 2 equivalents of $Ti(OiPr)_4$ in ethanol and/or isopropanol as reaction solvent. In this embodiment, the stage of reduction preferably takes place in the presence of $LiBH_4$ and/or of $NaBH_4$ and/or of $KBH_4$ and the stage of hydrolysis preferably takes place in the presence of an aqueous solution of citric acid.

According to one embodiment, the stage of condensation takes place in the presence of 1 equivalent of $Ti(OiPr)_4$ in ethanol and/or isopropanol as reaction solvent and the stage of reduction preferably takes place in the presence of $LiBH_4$ and/or of $KBH_4$.

At the end of this reaction of reductive amination, ferroquine (F) or its metabolite (Fm) is formed in the form of free base or of salt, for example of salt of dihydrochloride.

Ferroquine in the crude form can be isolated and purified according to techniques known by a person skilled in the art. The isolation of crude ferroquine at the end of the method of synthesis according to the invention, can be done by crystallization in a suitable solvent. Acetone, toluene, isopropanol or methyl ethyl ketone may be mentioned. Advantageously, it is acetone or toluene, even more advantageously it is toluene.

The method of synthesis according to the invention has the advantage relative to the prior art of being shorter if we consider the number of reaction stages and having better performance in terms of yield and productivity. Accordingly, it makes it possible to lower the final cost price of ferroquine through the use of inexpensive reagents, a reduction in the number of reaction stages relative to the route of synthesis currently used and represented in scheme 1 above and obtaining particularly advantageous reaction yields: the isolated yield of crude ferroquine is about 70-75 mol % relative to the starting aldehyde-amino ferrocene of formula (III).

Moreover, it offers the advantage of being safer with the absence of reagents or intermediates that may prove dangerous to handle.

The invention will now be described in more detail.

The following procedures and examples describe the preparation of intermediates of ferroquine and of ferroquine according to the invention. These procedures and examples are not limiting and their only purpose is to illustrate the present invention.

In the procedures and examples below:

The NMR (nuclear magnetic resonance) spectra are obtained with a Fourier transform spectrometer (BRUKER), at a temperature of 300° K (exchangeable protons not recorded);

s=singlet,
d=doublet,
m=multiplet,
br=broad signal,
t=triplet,
q=quadruplet,

DMSO-d$_6$=deuterated dimethylsulfoxide,
CDCl$_3$=deuterated chloroform;
The NMR spectra confirm the structures of the compounds obtained according to examples below.
In the examples given below, the following abbreviations are used:
MTBE: Tert-Butyl-Methyl-Ether
LiBH$_4$: lithium borohydride
NaBH$_4$: sodium borohydride
KBH$_4$: potassium borohydride
Ti(OiPr)$_4$: tetraisopropoxy-titanium
DMF: N,N-dimethylformamide
4,7-DCQ: 7-chloroquinolin-4-amine
MeOH: methanol
EtOH: ethanol
MEK: methyl ethyl ketone
tBuLi: t-butyllithium
DCM: dichloromethane
RT: room temperature
pTSA: para-toluenesulfonic acid
MP: melting point in ° C.

The mixtures of solvents are quantified in volume ratios, ml signifying milliliter.

In the following procedures, the starting compounds and the reagents, when their method of preparation is not described, are commercially available or are described in the literature, or else can be prepared according to methods described or known by a person skilled in the art.

Preparations

1. Preparation of the Compounds of Formula (III)

Preparation of 1-[(dimethylamino)methyl]-2-formyl-ferrocene.

Charge an inertized reactor with 39.6 g of 1-[(dimethylamino)methyl]-ferrocene and 360 ml of MTBE. Distill about 160 ml of MTBE (4V) at atmospheric pressure. Cool the solution to −10° C. and slowly add 98.2 ml of a solution of t-BuLi in heptane (titer 16%). Stir the reaction mixture at −10° C. for 2 hours and then at 0° C., slowly add 25.2 ml of DMF. Continue stirring the reaction mixture at 20° C. for 2 hours then at 5° C., slowly add 135 ml of 1.5N aqueous HCl. Continue stirring the reaction mixture at 5° C. for 30 min, then at 20° C. for 30 min. Leave the reaction mixture to settle and withdraw the aqueous phase then the MTBE phase. Counter-extract the aqueous phase with 125 ml of MTBE. Filter the combined MTBE phases on activated charcoal then concentrate to 120 ml under vacuum. Add 80 ml of isopropanol then distill 420 ml of solvent to constant volume, under vacuum, by regular addition of isopropanol. At the end of distillation, dilute the reaction mixture to 280 ml with isopropanol. 39.9 g of the expected compound is obtained in solution in isopropanol.

2. Preparation of 7-chloroquinolin-4-amine 2.1 Preparation of 7-chloroquinolin-4-amine Stir a mixture of 100 g of 4,7-DCQ and 1 liter of 5% solution of ammonia in methanol at 160° C. for at least 15 hours. After complete conversion of the 4,7-DCQ, concentrate the reaction mixture to 300 ml then slowly add 400 ml of a dilute aqueous solution (3.2%) of soda. Filter the suspension on a Büchner and rinse the cake with 100 ml of a water/MeOH mixture (70/30, v/v), then with 100 ml of water. Dry the beige solid in a stove at 100° C. under vacuum. 85.5 g of the expected compound is obtained.
MP=187° C. (with decomposition).

2.2 Purification of 7-chloroquinolin-4-amine

Heat a mixture of 85 g of the compound obtained in the preceding stage and 550 ml of toluene under reflux until complete dissolution then cooled slowly to 20° C. Filter the suspension on a Büchner. Rinse the cake with 85 ml of toluene then dry in a stove at 100° C. under vacuum. 76.8 g of the expected product is obtained.

EXAMPLES

The following procedures and examples describe the preparation of crude ferroquine from 7-chloroquinolin-4-amine and of 1-[(dimethylamino)methyl]-2-formyl-ferrocene (example 1 to 6) as well as the purification of said crude ferroquine (example 7).

Example 1

Heat a mixture of 0.5 g of the compound from preparation 2.2, 0.76 g of the compound from preparation 1, 25 mg of ApTS and 5 ml of toluene under reflux and remove the water by azeotropic distillation for 16 h. Concentrate the reaction mixture under vacuum and take up in 10 ml of absolute EtOH. Add 0.21 g of NaBH$_4$ and stir the reaction mixture for 16 h. Concentrate the reaction mixture under vacuum then take up in 40 ml DCM and a mixture of 20 ml of water and 2 ml of ammonia 25%. Leave the mixture to settle then extract the aqueous phase 4 times in 20 ml of DCM. Combine and concentrate the organic phases under vacuum, and crystallize the residue in 20 ml of acetone. Filter the solid cold on a Büchner, rinse with 2 times 5 ml of cold acetone then dry in a stove under vacuum. 0.37 g of the expected compound is obtained. A second crystallization stream is recovered from the mother liquor and the wash liquor, from which crystallization stream 0.11 g of the expected compound is obtained.
MP=197° C.
$^1$H-NMR (DMSOd$_6$, 500 MHz): 2.15 (s, CH3, 6H), 2.92 (d, NCH2, 1H), 3.82 (d, NCH2, 1H), 4.05 (t, CH, 1H), 4.17 (s, CH, 5H), 4.19 (dd, CH, 1H), 4.28 (dd, NCH2, 1H), 4.31 (dd, CH, 1H), 4.38 (dd, NCH2, 1H), 6.67 (d, CH, 1H) 7.48 (dd, CH, 1H), 7.75 (dd, NH, 1H), 7.78 (d, CH, 1H), 7.85 (d, CH, 1H), 8.42 (d, CH, 1H).

Example 2

Put 3.3 g of the compound from preparation 2.2, 5 g of the compound from preparation 1 and 50 ml of isopropanol in a flask. Add 10.9 ml of Ti(OiPr)$_4$. Stir the reaction mixture at RT for 24 h. Cool the reaction mixture to 0° C. and add 0.4 g of LiBH$_4$ in portions at 0° C. Stir the reaction mixture allowing the temperature to rise to RT for 16 h, then dilute with 50 ml of DCM. Pour this solution onto 40 ml of an aqueous solution of ammonia at 12.5%. After 30 minutes of stirring, filter the suspension on Clarcel®. Then rinse the cake with 6 times 20 ml of DCM. Wash the organic phase with 30 ml of 1N soda then concentrate under vacuum to 40 ml. Effect a change of solvent DCM/acetone by distillation at constant volume. Cool the suspension under reflux of the ketone at 5° C. Filter the solid on a Büchner, rinse with 2 times 9 ml of cold acetone and dry in a stove under vacuum. 4.2 g of the expected compound is obtained.

Example 3

Put 13.4 g of the compound from preparation 2.2 and 152.2 g of the compound from preparation 1 at 13.5% in isopropanol in a reactor. Add 42.8 g of Ti(OiPr)$_4$. Stir the reaction mixture at 25° C. for at least 20 h. Then put 5.7 g of finely divided NaBH$_4$ and 60 ml of isopropanol in a second reactor and cool to 0° C. Slowly pour the solution of imine intermediate onto this suspension of NaBH$_4$ at 0° C. Stir the reaction mixture at 25° C. for at least 20 h, concentrate under vacuum then dilute with 150 ml of DCM. Cool the solution obtained to 0° C. then hydrolyze at 0° C. with 60 ml of an aqueous solution of ammonia at 25%. Return the suspension to 20° C. then filter on Clartex. Rinse the cake with 5 times 20 ml of DCM. Concentrate the organic phase under vacuum to 200 ml. Effect a change of solvent DCM/acetone by distillation at constant volume. Cool the suspension under reflux of the ketone at 5° C. Filter the solid on a Büchner, rinse with 2 times 20 ml of cold acetone and dry in a stove under vacuum. 23.1 g of the expected compound is obtained.

Example 4

Put 13.2 g of the compound from preparation 2.2 and 125 g of a 16% solution of the compound from preparation 1 in isopropanol in a reactor. Add 42.0 g of Ti(OiPr)$_4$. Stir the reaction mixture at 25° C. for at least 20 hours. Put 8.0 g of KBH$_4$ and 60 ml of isopropanol in a second reactor and cool to 0° C. Slowly pour the solution of imine intermediate onto this suspension of KBH$_4$ at 0° C. Stir the reaction mixture at 25° C. for at least 20 h, concentrate under vacuum then dilute with 130 ml of DCM. Cool the solution obtained to 0° C. then hydrolyze at 0° C. with 60 ml of an aqueous solution of ammonia at 25%. Allow the temperature of the suspension to rise to 20° C. then filter on textile fiber; rinse the cake with 5 times 20 ml of DCM. Concentrate the organic phase under vacuum to 100 ml. Effect a change of solvent DCM/acetone by distillation at constant volume. Cool the suspension under reflux of the ketone at 5° C. Filter the solid on a Büchner, rinse with 2 times 20 ml of cold acetone and dry in a stove under vacuum. 23.1 g of the expected compound is obtained.

Example 5

Put 26.3 g of the compound from preparation 2.2 and 227 g of a solution of the compound from preparation 1 at 17.4% in isopropanol in a reactor. Add 83.8 g of Ti(OiPr)$_4$. Stir the reaction mixture at 40° C. for at least 5 hours. Put 15.9 g of KBH$_4$ and 120 ml of isopropanol in a second reactor and cool to 0° C. Slowly pour the solution of imine intermediate onto this suspension of KBH$_4$ at 0° C. Then stir the reaction mixture at 25° C. for at least 20 h, then heat at 50° C. for at least 3 h. Hydrolyze the reaction mixture at 20° C. by slowly adding 500 g of an aqueous solution of citric acid at 11.3%, then 75 g of an aqueous solution of ammonia at 20%. Add 400 ml of toluene, stir the reaction mixture at 50° C. for 30 min. Leave the organic phase to settle at 50° C., wash at 50° C. with 3 times 120 ml of water then filter on activated charcoal. Concentrate the organic phase under vacuum to 400 ml, then distill under vacuum to constant volume by adding 1 liter of toluene. Heat the toluene phase at 90° C. until completely dissolved then cool to 5° C. Filter the solid on a Büchner, rinse with 40 ml of cold MEK and dry in a stove under vacuum. 47.5 g of the expected compound is obtained.

Example 6

Put 26.3 g of the compound from preparation 2.2 and 217 g of a solution of the compound from preparation 1 at 18.4% in isopropanol in a reactor. Add 41.9 g of Ti(OiPr)$_4$. Stir the reaction mixture at 40° C. for at least 8 h. Put 15.9 g of KBH$_4$ and 120 ml of isopropanol in a second reactor and cool to 0° C. Slowly pour the solution of imine intermediate onto this suspension of KBH$_4$ at 0° C. Stir the reaction mixture at 20° C. for at least 20 h, then heat at 50° C. for at least 3 h. Hydrolyze the reaction mixture at 20° C. by slowly adding 320 g of an aqueous solution of citric acid at 13.2%, then 56 g of an aqueous solution of ammonia at 20%. Add 400 ml of toluene, then stir the reaction mixture at 50° C. for 30 min. Leave the organic phase to settle at 50° C., wash at 50° C. with 3 times 120 ml of water then filter on activated charcoal. Concentrate the organic phase under vacuum to 400 ml, then distill under vacuum to constant volume by adding 1 liter of toluene. Heat the toluene phase at 90° C. until completely dissolved then cool to 5° C. Filter the solid on a Büchner, rinse with 2 times 40 ml of cold MEK and dry in a stove under vacuum. 50.7 g of the expected compound is obtained.

Example 7

Put 24.0 g of crude ferroquine and 345 ml of MEK in a reactor and heat to 78° C. Cool the solution to 67° C. and initiate by adding 0.24 g of ferroquine in suspension in 1.2 ml MEK. Stir the mixture for 1 hour at 67° C. then cool to 10° C. Filter the suspension at 10° C. on a Büchner then wash the cake with 48 ml of MEK. Dry the solid in a stove under vacuum. 20.2 g of the expected compound is obtained.

What is claimed is:

1. A method of synthesis of ferroquine of formula (F) or of its metabolite of formula (Fm):

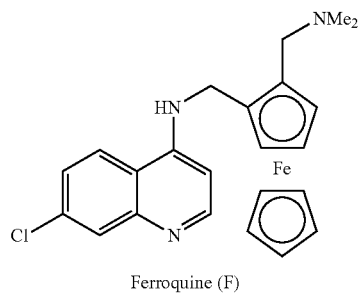

Ferroquine (F)

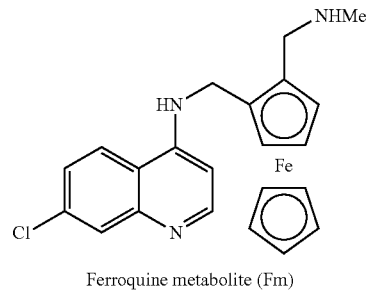

Ferroquine metabolite (Fm)

comprising a reaction of reductive amination in a reaction solvent, in which reaction:

(i) an aldehyde-amino ferrocene of formula (III),

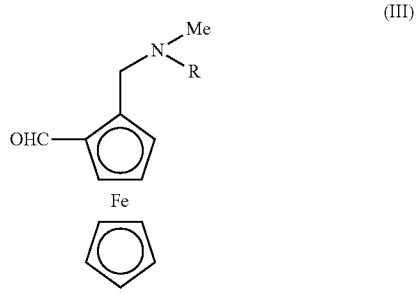

in which R represents a hydrogen atom or a methyl group, is condensed with 7-chloroquinolin-4-amine

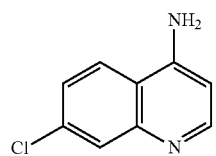 [SMILES: Nc1ccnc2cc(Cl)ccc12]

(ii) the product of condensation thus obtained of formula (II),

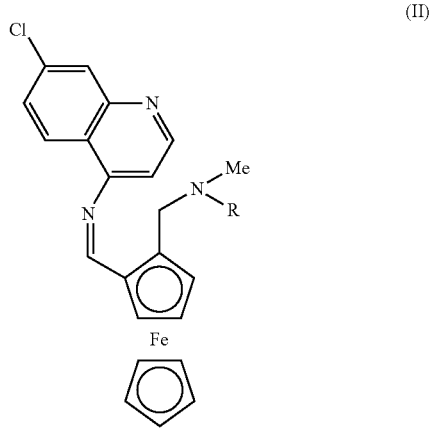

with R representing a hydrogen atom or a methyl group, is reduced in the presence of metal hydride, and (iii) the reaction mixture is hydrolyzed prior to isolation of the ferroquine of formula (F) or of its metabolite of formula (Fm).

2. The method as claimed in claim 1, wherein said compounds 7-chloroquinolin-4-amine and aldehyde-amino ferrocene of formula (III) are in stoichiometric proportion.

3. The method as claimed in claim 1, wherein the reaction of reductive amination takes place in the presence of at least one reaction solvent selected from ethanol, isopropanol, toluene, THF, dichloromethane and mixtures thereof.

4. The method as claimed in claim 1, wherein the stage of condensation of 7-chloroquinolin-4-amine with aldehyde-amino ferrocene of formula (III) takes place in the presence of:

at least one Lewis acid, or at least one Brønsted base or Brønsted acid.

5. The method as claimed in claim 1, wherein the stage of condensation of 7-chloroquinolin-4-amine with aldehyde-amino ferrocene of formula (III) takes place under azeotropic distillation of the reaction solvent of said stage of condensation or in the presence of at least one drying agent.

6. The method as claimed in claim 4, wherein the stage of condensation takes place in the presence of at least one Lewis acid selected from $Ti(OiPr)_4$, $TiCl_4$, $FeCl_3$, $ZnCl_2$, $AlCl_3$, $BF_3$, $BF_3.OEt_2$ and $BF_3.S(Me)_2$.

7. The method as claimed in claim 6, wherein the Lewis acid is $Ti(OiPr)_4$.

8. The method as claimed in claim 4, wherein the Lewis acid is used in stoichiometric amount or in excess.

9. The method as claimed in claim 8, wherein the Lewis acid is used in an amount between 1 and 2 equivalents.

10. The method as claimed in claim 4, wherein the stage of condensation takes place in the presence of at least one Brønsted acid or Brønsted base selected from acetic acid, trifluoroacetic acid, methanesulfonic acid, para-toluenesulfonic acid, $H_2SO_4$, $H_3PO_4$, $HNO_3$, piperidine and proline.

11. The method as claimed in claim 10, wherein the stage of condensation takes place in the presence of para-toluenesulfonic acid or piperidine.

12. The method as claimed in claim 5, wherein the drying agent is selected from alumina, molecular sieve 3 Å, $MgSO_4$ and $Na_2SO_4$.

13. The method as claimed in claim 1, wherein the stage of reduction takes place in the presence of metal hydrides selected from the borohydrides of sodium, potassium, lithium or zinc, optionally coupled to at least one additive selected from LiCl, $CaCl_2$, $MgCl_2$, $ZnCl_2$ and $NEt_3$.

14. The method as claimed in claim 13, wherein the borohydrides of sodium, potassium, lithium or zinc are selected from $NaBH(OAc)_3$, $NaBH_3CN$, $NaBH_4$, $KBH_4$, $LiBH_4$ and $Zn(BH_4)_2$.

15. The method as claimed in claim 14, wherein the reduction reaction takes place in the presence of $NaBH_4$, $KBH_4$ or $LiBH_4$.

16. The method as claimed in claim 1, wherein the stage of condensation takes place in the presence of para-toluenesulfonic acid, under azeotropic distillation of the reaction solvent.

17. The method as claimed in claim 16, wherein the reaction solvent is toluene.

18. The method as claimed in claim 16, wherein the stage of reduction takes place in the presence of $NaBH_4$.

19. The method as claimed in claim 1, wherein the stage of condensation takes place in the presence of titanium tetraisopropylate and of isopropanol as reaction solvent.

20. The method as claimed in claim 1, wherein the stage of condensation takes place in the presence of 1 equivalent of $Ti(OiPr)_4$ in ethanol, isopropanol or mixtures thereof as reaction solvent and the stage of reduction takes place in the presence of $LiBH_4$, $KBH_4$ or mixtures thereof.

21. The method as claimed in claim 1, wherein the stage of hydrolysis takes place in the presence of an aqueous solution of citric acid.

* * * * *